(12) United States Patent
Vivenzio et al.

(10) Patent No.: US 11,399,709 B2
(45) Date of Patent: Aug. 2, 2022

(54) SPECULUM TIP ELEMENT AND METHOD FOR OPTIMIZING LIGHT EFFICIENCY/EMISSION OF A SPECULUM TIP ELEMENT

(71) Applicant: Welch Allyn, Inc., Skaneateles Falls, NY (US)

(72) Inventors: Robert L. Vivenzio, Auburn, NY (US); Raymond A. Lia, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 213 days.

(21) Appl. No.: 16/820,000

(22) Filed: Mar. 16, 2020

(65) Prior Publication Data

US 2020/0297204 A1    Sep. 24, 2020

Related U.S. Application Data

(60) Provisional application No. 62/819,740, filed on Mar. 18, 2019.

(51) Int. Cl.
*A61B 1/227* (2006.01)
*A61B 1/06* (2006.01)

(52) U.S. Cl.
CPC ............... *A61B 1/227* (2013.01); *A61B 1/06* (2013.01)

(58) Field of Classification Search
CPC .................................. A61B 1/227; A61B 1/32
USPC .................................................. 600/201–245
See application file for complete search history.

(56) References Cited

U.S. PATENT DOCUMENTS

| 3,848,587 | A | 11/1974 | McDonald |
| 5,080,465 | A * | 1/1992 | Laude ................. G02B 5/1866 216/24 |
| 7,354,399 | B2 | 4/2008 | Strom et al. |
| 8,197,403 | B2 | 6/2012 | Strom et al. |

(Continued)

FOREIGN PATENT DOCUMENTS

WO    WO 2018/049480 A1    3/2018

OTHER PUBLICATIONS

Paul Waldron, "Surface Roughness Comparison" (May 2016) https://edmprecision.com/surface-roughness-comparison/ (Year: 2016).*

(Continued)

*Primary Examiner* — Eduardo C Robert
*Assistant Examiner* — Tara Rose E Carter
(74) *Attorney, Agent, or Firm* — Barclay Damon LLP

(57) ABSTRACT

An otoscopic tip element having an axisymmetric hollow body having a substantially conical shape and made from a moldable plastic material includes a distal opening, a proximal opening, an interior surface, and an exterior surface. To maximize light transmissivity, a distal portion of the interior surface is provided with a smooth or polished surface finish and a proximal portion of the interior surface and the outer surface is provided with a textured surface finish such that light from a light source of an otoscope can be axially directed through the hollow body for emission through the distal opening, as well circumferentially through the exterior surface. The surface finish and color/tint of the speculum tip element can be adjusted or tuned to promote axial, circumferential and total light output relative to an intended medical target.

16 Claims, 22 Drawing Sheets

(56) References Cited

U.S. PATENT DOCUMENTS

| | | | |
|---|---|---|---|
| 8,792,951 B1* | 7/2014 | Mao | A61B 5/1459 |
| | | | 600/340 |
| 2005/0027168 A1* | 2/2005 | Strom | A61B 1/227 |
| | | | 600/200 |
| 2006/0120432 A1* | 6/2006 | Lantz | G01J 5/021 |
| | | | 374/208 |
| 2006/0256575 A1* | 11/2006 | Vayser | A61B 1/303 |
| | | | 362/573 |
| 2010/0113886 A1* | 5/2010 | Piskun | A61B 17/0218 |
| | | | 600/231 |
| 2011/0160595 A1* | 6/2011 | Stone | A61B 1/06 |
| | | | 600/474 |
| 2016/0374546 A1 | 12/2016 | Berbee et al. | |

OTHER PUBLICATIONS

European Search Report for EP 20 163 772.5; Dated: Aug. 5, 2020; 7 pages.
European Search Report for EP 20 163 772.5; Dated: Jan. 18, 2022; 4 pages.

* cited by examiner

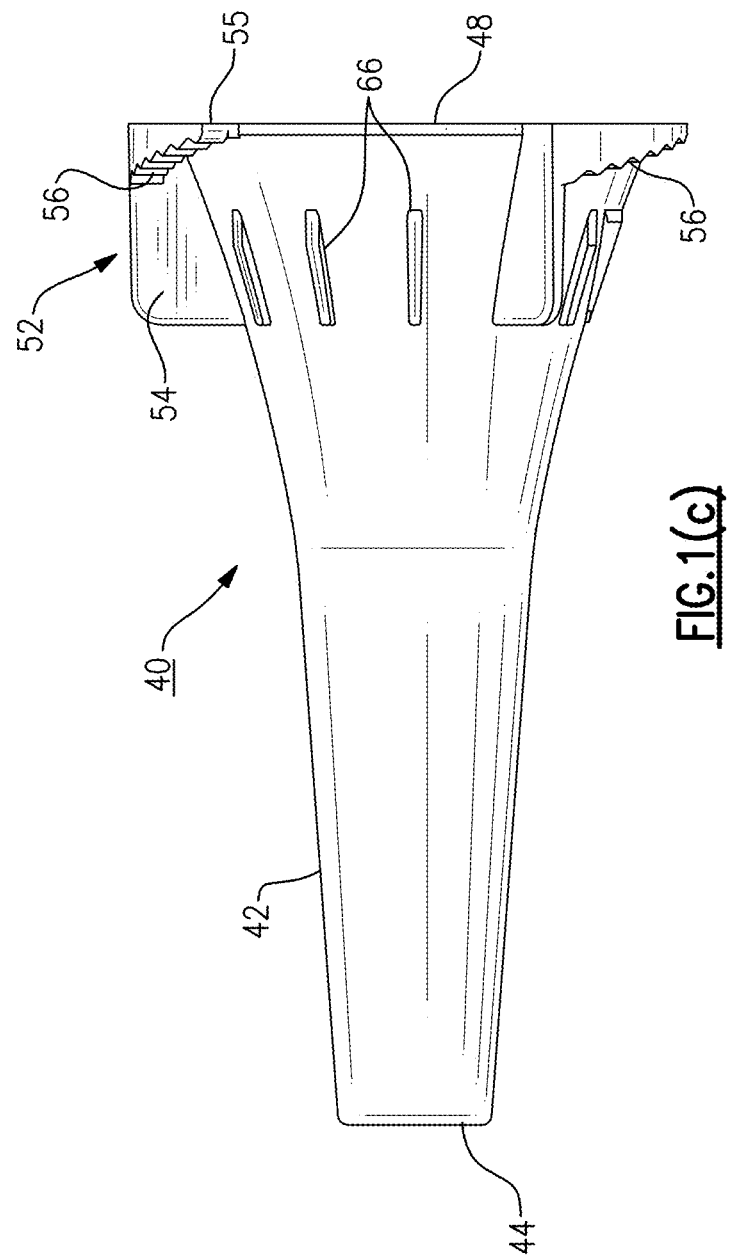

| Otoscope tip | lumens tip end | lumens total (fiber end) | side lumens |
|---|---|---|---|
| no tip | - | 15.54 | - |
| black (control) 1 | 2.98 | 2.86 | -0.12 |
| black (control) 2 | 2.97 | 2.85 | -0.12 |
| black (control) 3 | 2.94 | 2.82 | -0.12 |
| black (control) 4 | 2.86 | 2.74 | -0.12 |
| black (control) 5 | 2.75 | 2.64 | -0.11 |
| black (control) 6 | 1.81 | 1.74 | -0.07 |
| black (control) 7 | 2.18 | 2.10 | -0.08 |
| black (control) 8 | 2.90 | 2.78 | -0.12 |
| black (control) 9 | 2.52 | 2.41 | -0.11 |
| black (control) 10 | 2.25 | 2.17 | -0.08 |
| no tip | - | 15.27 | - |
| no tip Δ | - | 0.27 | - |

| | | | |
|---|---|---|---|
| Ave | 2.62 | 2.51 | -0.11 |
| Std dev | 0.409 | 0.389 | 0.020 |
| max | 2.98 | 2.86 | -0.07 |
| min | 1.81 | 1.74 | -0.12 |

| | | | |
|---|---|---|---|
| % of tip light output | 17.1% | - | - |
| % of total light output | - | 16.4% | -0.7% |

FIG. 7(a)

| Otoscope tip | lumens tip end | lumens total (fiber end) | side lumens |
|---|---|---|---|
| no tip | - | 15.36 | - |
| Trans Green 1 | 5.82 | 9.20 | 3.38 |
| Trans Green 2 | 6.15 | 9.53 | 3.38 |
| Trans Green 3 | 5.86 | 9.15 | 3.29 |
| Trans Green 4 | 5.72 | 8.97 | 3.25 |
| Trans Green 5 | 5.31 | 8.83 | 3.52 |
| Trans Green 6 | 6.18 | 9.54 | 3.36 |
| Trans Green 7 | 5.85 | 9.18 | 3.33 |
| Trans Green 8 | 5.57 | 9.02 | 3.45 |
| Trans Green 9 | 5.46 | 8.87 | 3.41 |
| Trans Green 10 | 5.69 | 8.89 | 3.20 |
| no tip | - | 15.22 | - |
| no tip Δ | - | 0.14 | - |

| | | | |
|---|---|---|---|
| Ave | 5.76 | 9.12 | 3.36 |
| Std dev | 0.276 | 0.255 | 0.095 |
| max | 6.18 | 9.54 | 3.52 |
| min | 5.31 | 8.83 | 3.20 |

| | | | |
|---|---|---|---|
| % of tip light output | 37.9% | - | - |
| % of total light output | - | 59.9% | 22.1% |

FIG. 7(c)

| Otoscope tip | lumens tip end | lumens total (fiber end) | side lumens |
|---|---|---|---|
| no tip | - | 15.22 | - |
| Clear 1 | 11.45 | 12.19 | 0.74 |
| Clear 2 | 11.40 | 12.14 | 0.74 |
| Clear 3 | 11.02 | 11.76 | 0.74 |
| Clear 4 | 11.48 | 12.21 | 0.73 |
| Clear 5 | 10.90 | 11.63 | 0.73 |
| Clear 6 | 11.48 | 12.22 | 0.74 |
| Clear 7 | 11.24 | 12.03 | 0.79 |
| Clear 8 | 11.42 | 12.15 | 0.73 |
| Clear 9 | 10.97 | 11.72 | 0.75 |
| Clear 10 | 11.31 | 12.05 | 0.74 |
| no tip | - | 15.10 | - |
| no tip Δ | - | 0.12 | - |

| | | | |
|---|---|---|---|
| Ave | 11.27 | 12.01 | 0.74 |
| Std dev | 0.224 | 0.223 | 0.018 |
| max | 11.48 | 12.22 | 0.79 |
| min | 10.9 | 11.63 | 0.73 |

| | | | |
|---|---|---|---|
| % of tip light output | 74.6% | - | - |
| % of total light output | - | 79.5% | 4.9% |

FIG. 7(e)

| Otoscope tip | lumens tip end | lumens total (fiber end) | side lumens |
|---|---|---|---|
| no tip | - | 15.35 | - |
| Trans clear with mark 1 | 11.02 | 13.31 | 2.29 |
| Trans clear with mark 2 | 9.95 | 11.95 | 2.00 |
| Trans clear with mark 3 | 10.70 | 13.09 | 2.39 |
| Trans clear with mark 4 | 10.81 | 13.16 | 2.35 |
| Trans clear with mark 5 | 10.79 | 13.15 | 2.36 |
| Trans clear with mark 6 | 10.83 | 13.15 | 2.32 |
| Trans clear with mark 7 | 9.93 | 12.01 | 2.08 |
| Trans clear with mark 8 | 10.63 | 13.03 | 2.40 |
| Trans clear with mark 9 | 10.96 | 13.23 | 2.27 |
| Trans clear with mark 10 | 10.14 | 13.01 | 2.87 |
| no tip | - | 15.29 | - |
| no tip Δ | - | 0.06 | - |

| | | | |
|---|---|---|---|
| Ave | 10.58 | 12.91 | 2.33 |
| Std dev | 0.412 | 0.498 | 0.230 |
| max | 11.02 | 13.31 | 2.87 |
| min | 9.93 | 11.95 | 2.00 |

| | | | |
|---|---|---|---|
| % of tip light output | 69.2% | - | - |
| % of total light output | - | 84.4% | 15.3% |

FIG. 7(g)

| Otoscope tip | lumens tip end | lumens total (fiber end) | side lumens |
|---|---|---|---|
| no tip | - | 15.56 | - |
| Trans clear 1 (Pinniacle 1112) | 11.98 | 13.88 | 1.90 |
| Trans clear 2 (Pinniacle 1112) | 11.84 | 13.78 | 1.94 |
| Trans clear 3 (Pinniacle 1112) | 11.94 | 13.83 | 1.89 |
| Trans clear 4 (Pinniacle 1112) | 11.79 | 13.75 | 1.96 |
| Trans clear 5 (Pinniacle 1112) | 11.9 | 13.78 | 1.88 |
| Trans clear 6 (Pinniacle 1112) | 11.81 | 13.72 | 1.91 |
| Trans clear 7 (Pinniacle 1112) | 11.88 | 13.75 | 1.87 |
| Trans clear 8 (Pinniacle 1112) | 11.69 | 13.63 | 1.94 |
| Trans clear 9 (Pinniacle 1112) | 11.77 | 13.68 | 1.91 |
| Trans clear 10 (Pinniacle 1112) | 11.77 | 13.66 | 1.89 |
| no tip | - | 15.40 | - |
| no tip Δ | - | 0.16 | - |

| | | | |
|---|---|---|---|
| Ave | 11.84 | 13.75 | 1.91 |
| Std dev | 0.088 | 0.077 | 0.029 |
| max | 11.98 | 13.88 | 1.96 |
| min | 11.69 | 13.63 | 1.87 |

| | | | |
|---|---|---|---|
| % of tip light output | 76.9% | - | - |
| % of total light output | - | 89.3% | 12.4% |

FIG. 7(i)

Test Group I

| Otoscope tip | lumens tip end | lumens total (fiber end) | side lumens |
|---|---|---|---|
| no tip | 15.87 | | |
| CAV 134 - 1 | 12.40 | 14.11 | 1.71 |
| CAV 134 - 2 | 12.44 | 14.01 | 1.57 |
| CAV 134 - 3 | 12.21 | 13.98 | 1.77 |
| CAV 134 - 4 | 12.26 | 13.97 | 1.61 |
| CAV 134 - 5 | 12.25 | 13.95 | 1.70 |
| CAV 134 - 6 | 12.24 | 13.98 | 1.72 |
| CAV 134 - 7 | 12.36 | 13.93 | 1.67 |
| CAV 134 - 8 | 12.17 | 13.98 | 1.76 |
| CAV 134 - 9 | 12.25 | 13.92 | 1.66 |
| CAV 134 - 10 | 12.21 | 13.92 | 1.70 |
| no tip Retest | | 15.47 | |
| no tip Δ | | 0.40 | |

| | | | |
|---|---|---|---|
| Ave | 12.28 | 13.97 | 1.69 |
| Std dev | 0.080 | 0.060 | 0.06 |
| max | 12.443 | 14.112 | 1.77 |
| min | 12.175 | 13.916 | 1.57 |

| % of tip light output | 79.4% | | |
| % of total light output | | 90.3% | 10.9% |

FIG. 8(a)

VDI 30

| Otoscope tip | lumens tip end | lumens total (fiber end) | side lumens |
|---|---|---|---|
| no tip | | 15.79 | |
| CAV 46 - 1 | 12.01 | 13.80 | 1.82 |
| CAV 46 - 2 | 12.09 | 13.88 | 1.79 |
| CAV 46 - 3 | 12.04 | 13.81 | 1.78 |
| CAV 46 - 4 | 12.06 | 13.85 | 1.77 |
| CAV 46 - 5 | 12.07 | 13.77 | 1.70 |
| CAV 46 - 6 | 12.04 | 13.74 | 1.70 |
| CAV 46 - 7 | 12.05 | 13.77 | 1.72 |
| CAV 46 - 8 | 11.90 | 13.74 | 1.84 |
| CAV 46 - 9 | 11.85 | 13.76 | 1.91 |
| CAV 46 - 10 | 11.90 | 13.73 | 1.83 |
| no tip Retest | | 15.57 | |
| no tip Δ | | 0.22 | |

| Ave | 12.00 | 13.79 | 1.78 |
| Std dev | 0.084 | 0.051 | 0.07 |
| max | 12.091 | 13.88 | 1.91 |
| min | 11.852 | 13.725 | 1.70 |

| % of tip light output | 77.1% | | |
| % of total light output | | 88.5% | 11.5% |

FIG. 8(b)

VDI 31.5

| Otoscope tip | lumens tip end | lumens total (fiber end) | side lumens |
|---|---|---|---|
| no tip | | 15.86 | |
| CAV 136 - 1 | 12.26 | 13.92 | 1.66 |
| CAV 136 - 2 | 12.10 | 13.88 | 1.78 |
| CAV 136 - 3 | 12.13 | 13.85 | 1.73 |
| CAV 136 - 4 | 12.12 | 13.86 | 1.74 |
| CAV 136 - 5 | 12.02 | 13.84 | 1.82 |
| CAV 136 - 6 | 12.05 | 13.84 | 1.79 |
| CAV 136 - 7 | 12.07 | 13.81 | 1.74 |
| CAV 136 - 8 | 12.08 | 13.85 | 1.81 |
| CAV 136 - 9 | 11.96 | 13.83 | 1.88 |
| CAV 136 - 10 | 11.99 | 13.78 | 1.79 |
| no tip Retest | | 15.46 | |
| no tip Δ | | 0.39 | |

| Ave | 12.08 | 13.84 | 1.77 |
| Std dev | 0.086 | 0.037 | 0.06 |
| max | 12.260 | 13.9204 | 1.88 |
| min | 11.958 | 13.775 | 1.66 |

| % of tip light output | 78.1% | | |
| % of total light output | | 89.5% | 11.4% |

FIG. 8(c)

Test Group III

| Otoscope tip | lumens tip end | lumens total (fiber end) | side lumens |
|---|---|---|---|
| no tip | | 15.98 | |
| CAV 134-1 | 12.88 | 14.44 | 1.56 |
| CAV 134-2 | 12.85 | 14.37 | 1.52 |
| CAV 134-3 | 12.78 | 14.34 | 1.56 |
| CAV 134-4 | 12.73 | 14.24 | 1.53 |
| CAV 134-5 | 12.64 | 14.25 | 1.65 |
| CAV 134-6 | 12.85 | 14.28 | 1.44 |
| CAV 134-7 | 12.57 | 14.25 | 1.72 |
| CAV 134-8 | 12.83 | 14.30 | 1.45 |
| CAV 134-9 | 12.78 | 14.27 | 1.49 |
| CAV 134-10 | 12.81 | 14.25 | 1.44 |
| no tip Retest | | 15.51 | |
| no tip A | | 0.47 | |

| | | | |
|---|---|---|---|
| Ave | 12.77 | 14.31 | 1.54 |
| Std dev | 0.101 | 0.061 | 0.09 |
| max | 12.880 | 14.4408 | 1.72 |
| min | 12.567 | 14.248 | 1.44 |

| | |
|---|---|
| % of tip light output | 82.4% |
| % of total light output | 92.3% |

FIG. 9(a)

VDI 30

| Otoscope tip | lumens tip end | lumens total (fiber end) | side lumens |
|---|---|---|---|
| no tip | | 13.68 | |
| CAV 46-1 | 12.79 | 14.30 | 1.51 |
| CAV 46-2 | 13.60 | 14.12 | 1.51 |
| CAV 46-3 | 12.60 | 14.18 | 1.58 |
| CAV 46-4 | 12.71 | 14.18 | 1.47 |
| CAV 46-5 | 12.52 | 14.17 | 1.65 |
| CAV 46-6 | 12.55 | 14.16 | 1.61 |
| CAV 46-7 | 12.60 | 14.12 | 1.53 |
| CAV 46-8 | 12.60 | 14.08 | 1.48 |
| CAV 46-9 | 12.60 | 14.09 | 1.60 |
| CAV 46-10 | 12.63 | 14.10 | 1.67 |
| no tip Retest | | 13.49 | |
| no tip A | | 0.19 | |

| | | | |
|---|---|---|---|
| Ave | 12.59 | 14.15 | 1.56 |
| Std dev | 0.105 | 0.066 | 0.07 |
| max | 12.798 | 14.304 | 1.67 |
| min | 12.436 | 14.081 | 1.47 |

| | |
|---|---|
| % of tip light output | 81.3% |
| % of total light output | 91.3% |

FIG. 9(b)

VDI 31.5

| Otoscope tip | lumens tip end | lumens total (fiber end) | side lumens |
|---|---|---|---|
| no tip | | 13.60 | |
| CAV 136-1 | 12.55 | 14.25 | 1.70 |
| CAV 136-2 | 12.77 | 14.19 | 1.48 |
| CAV 136-3 | 12.53 | 14.12 | 1.59 |
| CAV 136-4 | 12.55 | 14.17 | 1.63 |
| CAV 136-5 | 12.52 | 14.13 | 1.61 |
| CAV 136-6 | 12.59 | 14.13 | 1.56 |
| CAV 136-7 | 12.48 | 14.08 | 1.60 |
| CAV 136-8 | 12.50 | 14.08 | 1.57 |
| CAV 136-9 | 13.13 | 14.12 | 1.93 |
| CAV 136-10 | 12.48 | 14.08 | 1.60 |
| no tip Retest | | 13.48 | |
| no tip A | | 0.32 | |

| | | | |
|---|---|---|---|
| Ave | 12.59 | 14.14 | 1.63 |
| Std dev | 0.131 | 0.054 | 0.12 |
| max | 12.798 | 14.245 | 1.93 |
| min | 12.186 | 14.076 | 1.48 |

| | |
|---|---|
| % of tip light output | 80.8% |
| % of total light output | 93.3% |

FIG. 9(c)

VDI 33

Test Group III

VDI 30

| Otoscope tip | lumens tip end | lumens total (fiber end) | side lumens |
|---|---|---|---|
| no tip | - | 15.98 | - |
| CAV 134 - 1 | 12.23 | 13.90 | 1.68 |

FIG. 10(a)

VDI 31.5

| Otoscope tip | lumens tip end | lumens total (fiber end) | side lumens |
|---|---|---|---|
| no tip | - | 15.88 | - |
| CAV 46 - 1 | 12.16 | 13.75 | 1.59 |

FIG. 10(b)

VDI 33

| Otoscope tip | lumens tip end | lumens total (fiber end) | side lumens |
|---|---|---|---|
| no tip | - | 15.80 | - |
| CAV 136 - 1 | 12.08 | 13.78 | 1.70 |

FIG. 10(c)

SPECULUM TIP ELEMENT AND METHOD FOR OPTIMIZING LIGHT EFFICIENCY/EMISSION OF A SPECULUM TIP ELEMENT

CROSS REFERENCE TO RELATED APPLICATION

This application claims priority to U.S. Ser. No. 62/819,740, filed Mar. 18, 2019, under applicable portions of 35 U.S.C. § 119 and 35 U.S.C. § 120, the entire contents of which are incorporated by reference.

TECHNICAL FIELD

This application is generally directed to the field of diagnostic medicine and more specifically to the design and manufacture of a single use or single patient speculum tip element intended for use in conjunction with a medical diagnostic device, such as an otoscope. The speculum tip element is made from a moldable plastic material in which surface clarity and finish/texture characteristics are tuned and optimized in order to control or maximize axial and/or circumferential light transmission relative to a medical target of interest.

BACKGROUND

Speculum tip elements are well known in the field of diagnostic medicine, particularly for use in otoscopic instruments (otoscopes) to enable examinations of the ear of a human or veterinary subject. Usually the speculum tip element, which is hollow and defined by an axisymmetric configuration including a substantially conical shape, is releasably attached to the distal end of the instrument head of the otoscope. The attached speculum tip element is sized to be fitted only to a predetermined distance within the ear canal of the subject in order to prevent injury. The output of a light source contained within the otoscope is directed by means of a bundle of optical fibers to the distal end of the instrument head and transmitted through a tip opening of the attached speculum tip element to facilitate viewing of the intended medical target (e.g., the tympanic membrane). Examples of an otoscopic system that includes the above speculum tip element is U.S. Pat. Nos. 7,354,399 and 8,197,403, each of which are incorporated by reference in their entirety.

While some speculum tip elements are reusable, a high percentage of commercially sold speculum tip elements are disposable and therefore only intended for single patient or single use.

Traditional disposable speculum tip elements are molded from a plastic material having a black colorant additive to prevent light losses through the exterior of the speculum tip element. Additionally, these speculum tip elements are further defined by a smooth and polished inner surface. The smooth or polished inner surface promotes consistent light transmission for emission as light from the contained light source as the light is directed through the attached speculum tip element toward the subject's ear.

In the field, there have been significant advances in light source technology for medical diagnostic devices including otoscopes. LEDs provide an effective alternative to traditional incandescent bulbs due to their increased product life. In addition, LEDs do not build up excess heat that requires the inclusion of dissipation features for thermal management, such as heat sinks, radiating fins and the like. LEDs also enable the transmission of light of different wavelengths and different color temperatures, which can enhance or improve the quality of medical examinations. These advances have added to an existing and general need in the field to be able to more effectively utilize the total amount of light from a light source, such as those retained in a medical diagnostic device.

In addition, there is a general need in the field of diagnostic medicine to provide greater versatility for handheld medical diagnostic instruments to enable patient examinations to be more effectively conducted. For example, otoscopes can be used to conduct examinations of medical targets other than the ear, including the throat and nose of a subject. To conduct these examinations, however, a traditional opaque (black colored) speculum tip element must first be removed from the instrument head to better provide illumination to those areas, since these speculum tip elements cannot provide peripheral illumination. That is, all of the illumination output (except light losses) is solely directed to the distal opening of the speculum tip element.

Still further, the use of traditional speculum tip elements makes it fairly difficult to determine whether the otoscope or other medical diagnostic device has been powered off following a patient examination. Usually, the device must first be picked up and the distal end must be rotated toward the user in order to determine that the device has actually been powered down. Failure to properly identify the power state of the instrument can lead to premature loss of battery life and inconvenience/delays for the practitioner/caregiver, as well as the patient.

BRIEF DESCRIPTION

Therefore and according to a first aspect, there is provided a method for adjusting light emissivity of a speculum tip element as used in conjunction with a medical diagnostic device. According to this method, the speculum tip element is fabricated from an optically clear plastic moldable material in which the surface finish or texture of the exterior surface of the speculum tip element is varied in order to maximize the output of illumination transmitted through a distal opening of the tip element, while also increasing or varying the amount of side or peripheral illumination. According to at least one version, the color of the speculum tip element can be adjusted to create different levels of translucence in order to produce a preferred axial or peripheral illumination, either alone or in combination with the surface finish.

Surprisingly, it has been determined that providing an optically clear speculum tip element with a roughened surface finish of the exterior surface can produce a greater amount of axial light transmission through the distal opening of the speculum tip element, as compared with a traditional opaque speculum tip element having a smooth or polished exterior surface finish. Still further, it has been determined that varying the surface finish of the exterior surface of the speculum tip element can also produce greater peripheral light transmission, while maintaining acceptable levels of illumination output at the distal opening of the speculum tip element.

According to another aspect, there is provided a speculum tip element comprising a hollow body defined by an axisymmetric and substantially conical shape including a distal tip opening, an interior surface and an exterior surface. The speculum tip element is made from a clear moldable plastic material whose properties are adjusted or tuned during manufacture in order to maximize or regulate the transmission of light from a coupled light source for emission through the distal tip opening, as well as peripherally or circumferentially through the outer or exterior surface of the tip element. According to at least one version, the exterior or interior surface of the speculum tip element can be manufactured with a surface finish or color that optimizes overall light transmission, as well as providing increased axial and/or peripheral illumination relative to a medical target of interest.

According to yet another version, there is provided a speculum tip element comprising a hollow body made from a moldable plastic material, a distal opening, a proximal opening, an interior surface, and an exterior surface. The hollow body is axisymmetric and defined by a substantially conical shape in which the distal opening has a diameter that is smaller than the diameter of the proximal opening. The interior surface of the speculum tip element has a smooth surface finish and the exterior surface has a roughened surface finish such that light from a light source of the otoscope can be axially directed through the hollow body for emission through the distal tip opening, as well as peripherally through the exterior surface.

Applicant has herein determined that variations in manufactured characteristics of a moldable speculum tip element can produce dramatic, tunable effects in terms of light transmission, both axially and peripherally. For example, it has been determined that a speculum tip element made from an optically clear or transparent material provides an increase in peripheral light transmission, but losses are created that result in less transmitted light at the distal opening. Surprisingly, however, providing a roughened surface finish on the exterior surface of the tip element maintains a relatively high amount of circumferential light transmission, but without significantly decreasing illumination output directed through the distal opening.

It addition, it has also been determined that adjusting the color or tint of the moldable plastic material of the speculum tip element, either alone or in combination with variations in surface finish, particularly the surface finish of the exterior surface, can further maximize or tune the amount of light transmission.

According to yet another version, there is provided a method for controlling the light transmissivity of a speculum tip element for an otoscope. This method includes the following steps: First, a speculum tip element is provided, the speculum tip element being made from a moldable plastic material that is at least optically translucent. The speculum tip element is defined by an axisymmetric hollow body having a distal opening, an opposing proximal opening, an exterior surface and an interior surface. The exterior surface of the speculum tip element is provided with a textured or roughened surface finish, and the interior surface of a distal portion of the speculum tip element is provided with a smooth or polished surface finish.

An otoscopic tip element having some degree of circumferential or peripheral light transmission can be advantageous, for example, when using a medical diagnostic device, such as an otoscope to illuminate medical targets other than the ear, such as the throat or nose of a subject. Moreover, the color or tint of the speculum tip element can more effectively enable visualization of features at the medical target of interest. For example, a speculum tip element having a green translucent color produces a glow that better visualizes certain medical surfaces.

Another advantage realized by the herein described speculum tip element and related method is that greater and more efficient light output can be transmitted. Accordingly, the amounts of axial and peripheral light transmission to be directed to a medical target of interest can be tuned or optimized. Furthermore, the amount of energy required to illuminate the light source(s) can also be optimized and therefore smaller power supplies would be required.

Yet another advantage is that enabling peripheral illumination of the speculum tip element provides the user of the medical diagnostic device with an indicator as to whether the medical diagnostic device had been powered off following a patient examination, thereby leading to less battery waste, longer product life and increased efficiency in the use of the device(s).

These and other technical features and advantages will be readily apparent from the following Detailed Description, which should be read in conjunction with the accompanying drawings.

BRIEF DESCRIPTION OF THE DRAWINGS

FIG. 1(c) is a side elevational view of the speculum tip element of FIGS. 1(a) and 1(b);

FIGS. 8(a), 8(b) and 8(c) present tabular data of light transmissivity of a Test Group I made up of various speculum tip elements having different surface finishes;

FIGS. 9(a), 9(b) and 9(c) present tabular data of light transmissivity of a Test Group II made up of various speculum tip elements having different surface finishes; and FIGS. 10(a), 10(b) and 10(c) present tabular data of light transmissivity of a Test Group III made up of various speculum tip elements having different surface finishes.

DETAILED DESCRIPTION

Figure 1A:
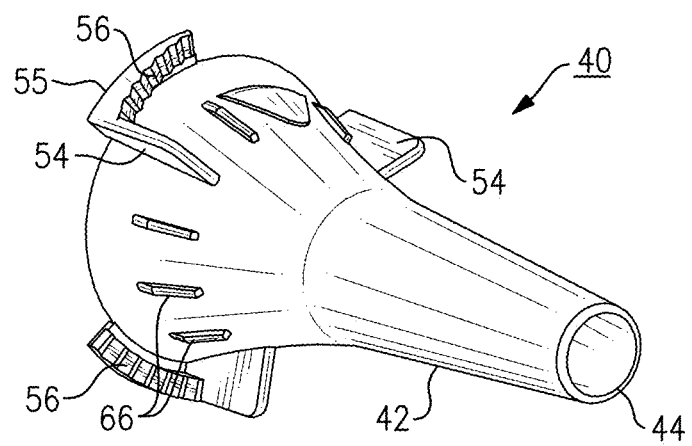
FIG. 1(a) is a front perspective view of a known speculum tip element.

The following relates to various embodiments of speculum tip elements for use in a medical diagnostic instrument, and more specifically an otoscope. A specific axisymmetric speculum tip element design and features are used throughout the following discussion. However, it will be understood that the described embodiments are examples and a myriad of modifications and variations are therefore possible. As described herein, certain characteristics of a plastic molded speculum tip element can be tuned or optimized at the time of manufacture in order to enhance light transmissivity, whether axially through the distal opening of the speculum tip element and/or circumferentially about the exterior (i.e., through the outer surface or peripherally) of a hollow speculum tip element body. Throughout the course of discussion, various terms such as "outer", "inner", "within", "interior", "exterior", "distal", "proximal" and the like are used in order to provide a suitable frame of reference in regard to the accompanying drawings. However, these terms are not intended to be over limiting of the scope of the invention, except where so specifically indicated. In addition, the accompanying drawings are intended to show the salient features of the invention. These drawings, however, are not intended to necessarily provide scaling or dimensional accuracy.

For purposes of the following description, the terms "clear" or "transparent" as used herein, commonly refer to a material that permits complete passage or transmission of light. The term "translucent" as used herein refers to a material that permits the passage or transmission of a portion of light. The terms "black" or "opaque" as used herein refers to a material that does not permit the passage of any light. The terms "roughened" or "textured" as used herein refers to a material surface finish that creates either an opaque or translucent condition. The term "smooth" or "polished", as used throughout, refers to a material surface finish that can create or maintain a transparent condition in the case of clear materials.

In terms of background, reference is first made to FIGS. 1(a)-1(d), which illustrates several views of a commercially known speculum tip element 40. The speculum tip element 40 according to this example is manufactured from a plastic material, such as polypropylene, using a molding process, which further includes a black colorant additive. As shown, the finished speculum tip element 40 is defined by a hollow body 42 having a axisymmetric configuration. More specifically, the body 42 has a truncated frusto-conical shape including a distal tip opening 44 and an opposing proximal tip opening 48. The diameter of the tip element 40 varies between a minimum diameter at the distal tip opening 44 and tapers consistently to a maximum diameter at the proximal tip opening 48. The range of diameters of the distal tip opening 44 can vary depending on the application and the patient. For example, a range of diameters can vary between about 1 mm and 10 mm, which are suitable for placement in the ear canal of most patients. The speculum tip element 40 is shaped and configured to be releasably attached to the distal axisymmetric insertion portion of an otoscope (not shown) wherein the tapered distal end of the attached speculum tip element 40 can be inserted up to a predetermined distance within the ear canal of the patient.

The herein described speculum tip element 40 further includes features to enable releasable attachment to the distal end and more specifically the distal insertion portion of the otoscopic instrument head (not shown), depending on the otoscope design. A plurality of engagement features 52 are circumferentially and evenly spaced about the exterior surface of the speculum tip element 40. According to this specific version, three (3) such features, equally spaced from one another circumferentially by about 120 degrees, as provided, though the actual number of engagement features provided could be suitably varied. Each of the external engagement features 52 extends radially from the open proximal end opening 48 of the tip element 40 and commonly includes a circumferential securing portion 55 and a depending axial portion 54 forming a substantially L-shape, the circumferential securing portion 55 having a plurality of teeth 56 that are located on an engagement surface thereof. Additionally, the circumferential securing portion 55 is substantially wedge-shaped, the securing portion 55 having a maximum thickness at the interface with the depending axial portion 54 and a tapered minimum thickness at an opposing end, thereby forming the ramped engagement surface. The depending axial portions 54 facilitate stacking of a plurality of tip elements 40, as well as provide a grip surface when attaching the tip elements to the otoscope. An additional number of spaced axial ribs 66 disposed between each of the depending axial portions aid in providing a gripping surface when attaching the tip elements 40.

Figure 1B:
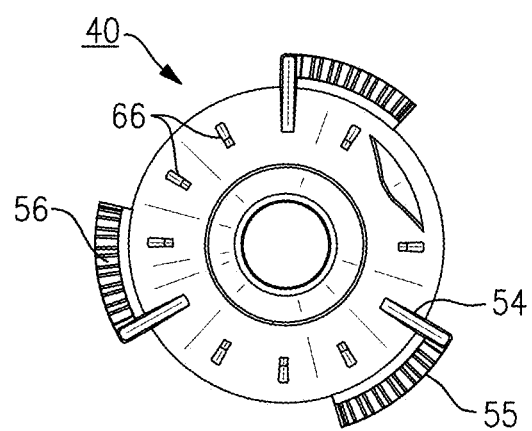
FIG. 1(b) is a front view of the speculum tip element of FIG. 1(a)
Figure 1D:
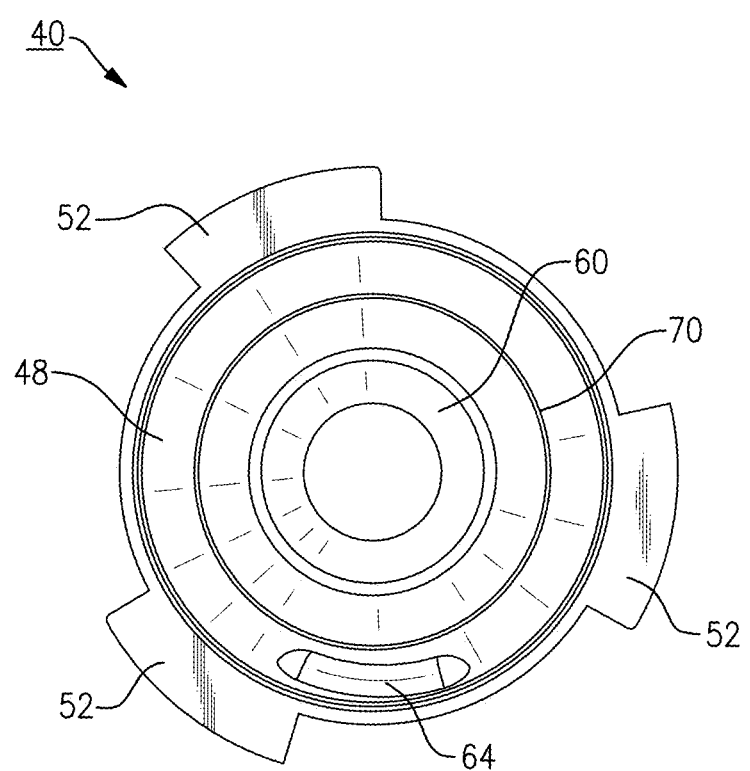
FIG. 1(d) is a rear view of the speculum tip element of FIGS. 1(a)-1(c)

With further reference to FIGS. 1(a)-1(d), the interior surface 60 of the herein described tip element 40 includes an angled interior protrusion 64 that is located near the proximal tip opening 48. Referring to FIG. 1(d), the tip element 40 also includes an interior annular sealing ring 70, which is provided to assist in sealing the tip element 40 to a conical portion of the distal axisymmetric insertion portion of the otoscope, preferably for insufflation purposes. These features are described in greater detail in U.S. Pat. No. 8,197,403, which is incorporated by reference in its entirety.

Figure 1E:
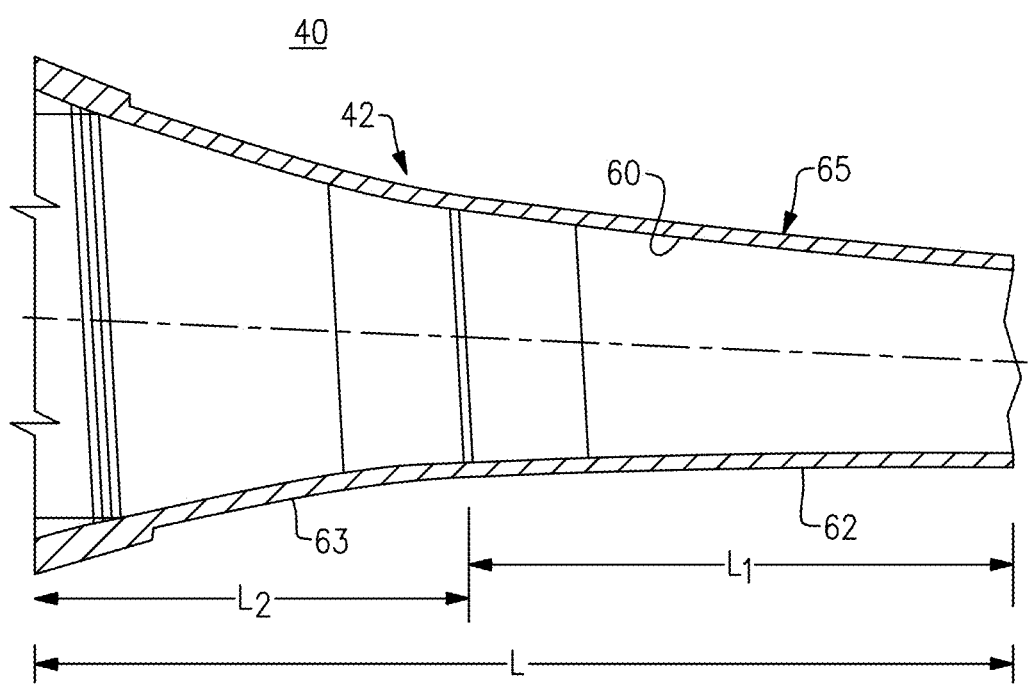
FIG. 1(e) is a side sectioned view of the speculum tip element of FIGS. 1(a)-1(d)

In terms of overall manufacture, the herein described otoscopic speculum tip element 40 is created using a molding process in which a black colored agent or additive is added to the polypropylene material. As shown in FIG. 1(e), a distal portion 62 of the interior surface 60 of the molded speculum tip element 40 is provided with a smooth and polished finish in order to avoid inconsistencies in the transmission of light. An adjacent proximal portion 63 of the interior surface 60, as well as the outer or exterior surface 65 of the tip element 40 is provided with a suitable surface texture or finish to permit the speculum tip element 40 to be removed from the mold. Typically, this surface finish is about VDI 32 as obtained from a VDI 3400 surface comparator. The overall length of the interior surface 60 is defined by length L, in which the proximal portion 63 is that portion of the interior surface 60, as defined by a length L2 that engages the distal insertion portion of an otoscope. The distal portion 62, which is defined by a corresponding length L1, encompasses the remaining portion of the interior surface 60, which as noted is polished as a smooth light carrying segment.

Figure 2:
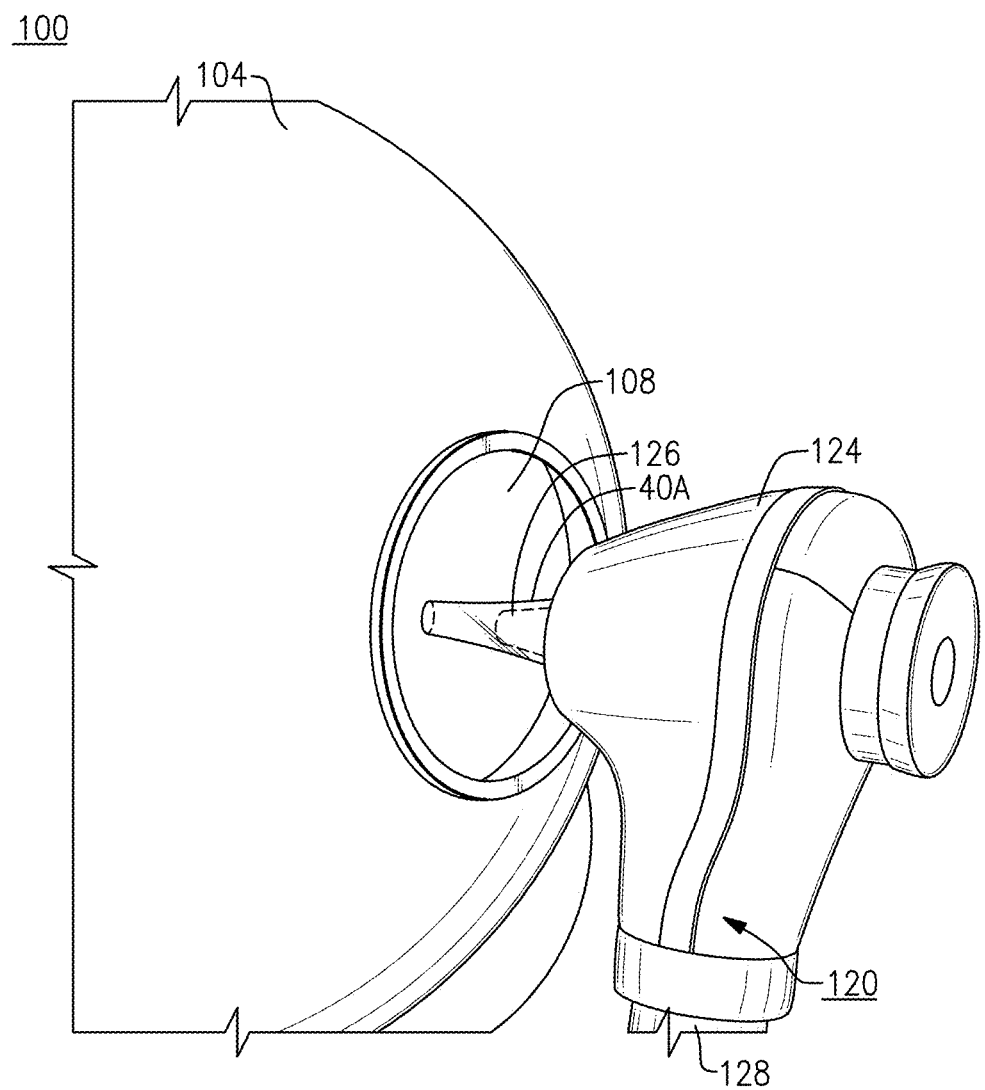
FIG. 2 is a partial perspective view of a test fixture used to measure light transmission of various groups of speculum tip elements, the tip elements being releasably attached to a medical diagnostic device.
Figure 3:
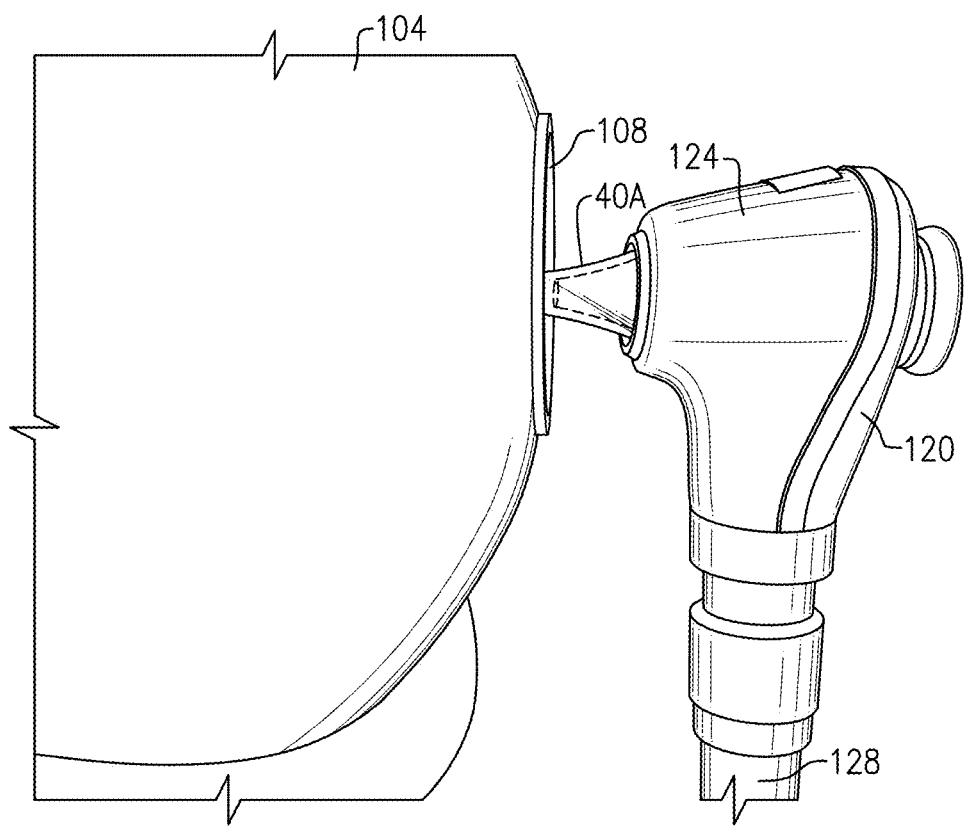
FIG. 3 is another partial view of the test fixture of FIG. 2 including a side view of a speculum tip element attached to the medical diagnostic device relative to the test fixture.

Various groups of axisymmetric speculum tip elements having the above structural design shown in FIGS. 1(a)-1(e) were tested in which a number of material properties were adjusted during manufacturing in order to determine their effect upon axial and peripheral light transmissivity. As shown in FIGS. 2 and 3, a test fixture 100 was created upon which various groups of speculum tip elements were individually tested. The test fixture 100 is defined by a hollow spherical integration chamber 104 having an external port 108. A spectrophotometer (not shown) is configured to measure light output. For purposes of the testing, it was necessary to be able to measure or at least deduce the illumination output at: i) the distal tip opening of an attached speculum tip element; and ii) the outer periphery of the attached speculum tip element.

Each speculum tip element was attached using the external engagement features 52, FIG. 1(b) to the distal axisymmetric insertion portion 126 of an instrument head 124 of a known otoscope 120. For purposes of this testing, the otoscope 120 is defined by an instrument head 124 having the distal axisymmetric insertion portion 126. The instrument head 124 is attached to the upper end of an instrument handle portion 126. An LED (not shown) is used as a light source, the latter being contained within the instrument 120 and whose light output is directed to the distal end of the insertion portion 126 by means of contained optical fibers (not shown). Further details relating to the otoscope 120 are provided in co-pending U.S. patent application Ser. No. 16/248,482, filed Jan. 15, 2019, the entire contents of which are incorporated by reference.

With further reference to FIGS. 2 and 3, the attached speculum tip element 40A was inserted through the external port 108 formed in the spherical integration chamber 104, wherein the test fixture 100 was configured to fixedly retain the handle portion 128 of the otoscope 120. The spectrophotometer (not shown) was configured to initially measure the illumination output at the distal tip opening of the speculum tip element 40 prior to inserting the speculum tip element 40A within the spherical integration chamber 104. Following this measurement, the spectrophotometer was configured to measure the total amount of lumens by placing the entire tip element 40A within the spherical integration chamber 104, FIG. 2, and then repositioning the otoscope 120 such that the fiber (distal) end of the otoscope 120 is substantially flush with the external port 108 of the chamber 104, as shown in FIG. 3. From the foregoing, the illumination output from the periphery of the speculum tip element 40A can be determined by subtracting the tip end illumination output from the fiber end illumination output.

As noted, multiple groups of specifically fabricated speculum tip elements 40A were tested. As previously noted and for purposes of this testing, each of the groups of speculum tip elements were commonly and structurally defined with the design attributes shown in FIGS. 1(a)-1(e), including an axisymmetric hollow body made from a moldable plastic material defined by a substantially conical shape including a distal tip opening, a proximal tip opening, an outer or exterior surface, and an inner or interior surface. As discussed in greater detail, each Test Group of speculum tip elements 40A were provided with different material and/or surface finish characteristics, each Test Group being described further described as follows:

A first set of speculum tip elements 200 (herein designated as Test Group A) comprise traditional speculum tip elements, such as described previously with reference to FIGS. 1(a)-1(e) and commercially sold under the tradename of Kleen Spec™ by Welch Allyn, Inc. of Skaneateles Falls, N.Y. These speculum tip elements 200, which were tested as control samples, are made from polypropylene and more specifically Profax 6523, having a black colorant additive such as #2P1147BP in pellet form, the latter being manufactured by Primary Colors, Inc. More specifically, the speculum tip elements 200 are defined by an interior surface having a polished distal portion 62, FIG. 1(e), a textured proximal portion 63, FIG. 1(e) and an exterior surface 65, FIG. 1(e), having an adequate surface finish sufficient to enable the speculum tip element 200 to be released from the mold. The textured proximal portion 63 of the interior surface 60, FIG. 1(e), of the speculum tip elements 200 and the exterior surface 65 of this Test Group A were fabricated with a surface finish of about 32 (31.5), as determined by a surface comparator based on VDI 3400.

Each of the second set of speculum tip elements 300 (herein designated as Test Group B) was also defined with all of the design attributes of the speculum tip elements 200 of Test Group A shown in FIGS. 1(a)-1(e). The speculum tip elements 300 of this Test Group, were made from the same polypropylene material (Profax 6523) as those of Test Group A, but in which the material of each speculum tip element has an optically translucent green color. As in the preceding, the interior surface 60, FIG. 1(e), includes a polished distal portion 62, FIG. 1(e), and a proximal portion 63, FIG. 1(e), with the proximal portion 63 of the interior surface 60 and the exterior surface 65, FIG. 1(e), having a surface finish of VDI 32 (31.5).

A third set of speculum tip elements 400 (herein designated as Test Group C) was also defined with all of the same structural design attributes as Test Groups A and B. The speculum tip elements 400 of this Test Group were also made from the same polypropylene material (Profax 6523) as Test Groups A and B, but in which the plastic material was clarified enabling the speculum tip elements 400 to be optically clear. In addition, both the entire interior and exterior surfaces 60, 65, FIG. 1(e), of the speculum tip elements 400 of this Test Group were polished with no surface texture in order to maintain the clear and transparent nature of the plastic material.

A fourth set of speculum tip elements 500 (herein designated as Test Group D) was defined with all of the same design attributes of the speculum tip elements 200, 300, 400 of the prior Test Groups A, B and C. However, the speculum tip elements of this Test Group were molded using the same clarified polypropylene material, (Profax 6523 homopolymer), that is further defined by an interior surface 60, FIG. 1(e), having a polished (no surface texture) distal portion 62, FIG. 1(e) and in which the proximal portion 63, FIG. 1(e) of the interior surface 60, FIG. 1(e), and the exterior surface 65, FIG. 1(e), of each speculum tip element 500 tested was provided with a textured surface finish. According to this embodiment, the surface finish of the proximal portion 63 of the interior surface 60 and the entire exterior surface 65 was about VDI 32 (31.5) with the distal portion 62 of the interior surface 60 being polished with a completely smooth surface texture.

Finally, a fifth set of speculum tip elements 600 (herein designated as Test Group E) was defined with all of the same design attributes of the speculum tip elements of the prior Test Groups A-D. The speculum tip elements 600 of this Test Group were intended to be identical to the speculum tip elements of Test Group D, including the same interior and exterior surface finishes/textures with the only difference between Test Groups D and E being the choice of plastic material. More specifically, the speculum tip elements 600 of this Test Group E were molded from another clarified polyethylene material (Pinnacle 1112).

For each of the speculum tip elements of Test Groups A, B, D and E, the surface finish of the proximal portion 63, FIG. 1(e), of the interior surface 60 and the exterior surface 65 was Moldtech (MT) 11010 or equivalent (surface finish of approximately VDI 32 (31.5)). A total of ten (10) sample tip elements were fabricated and tested for each of the five (5) Test groups (A-E) of speculum tip elements 200, 300, 400, 500, 600.

Figure 4:
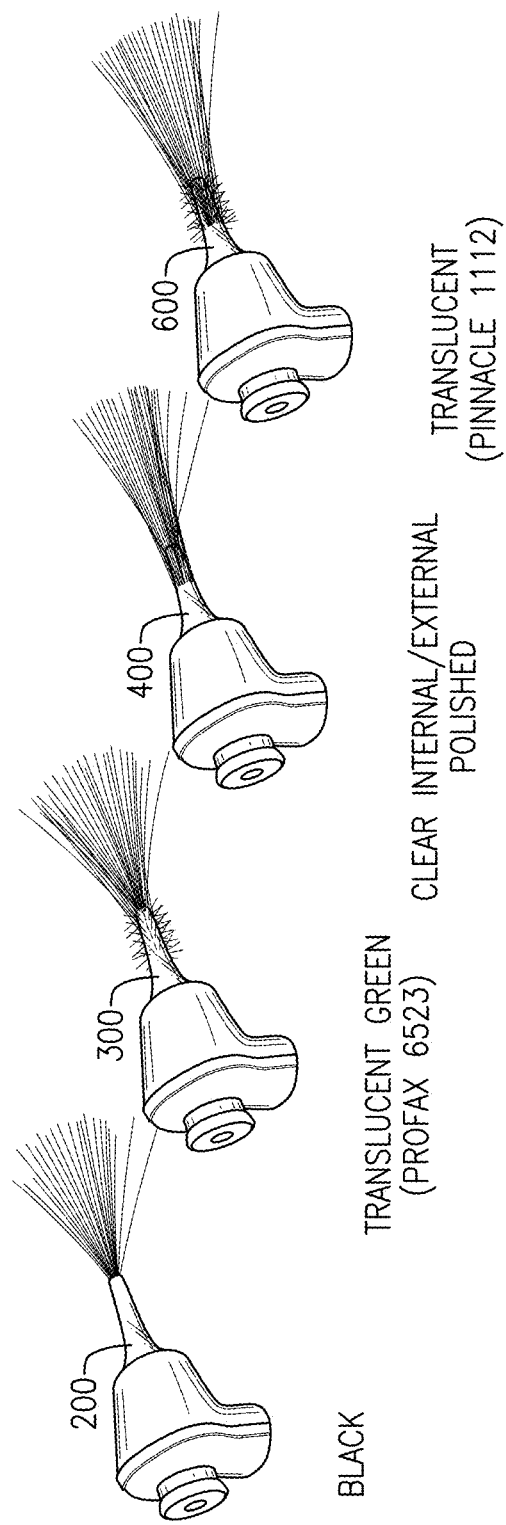
FIG. 4 is a perspective view depicting various light emission characteristics of tested speculum tip elements, including speculum tip elements made in accordance with various aspects of the present invention.
Figure 5:
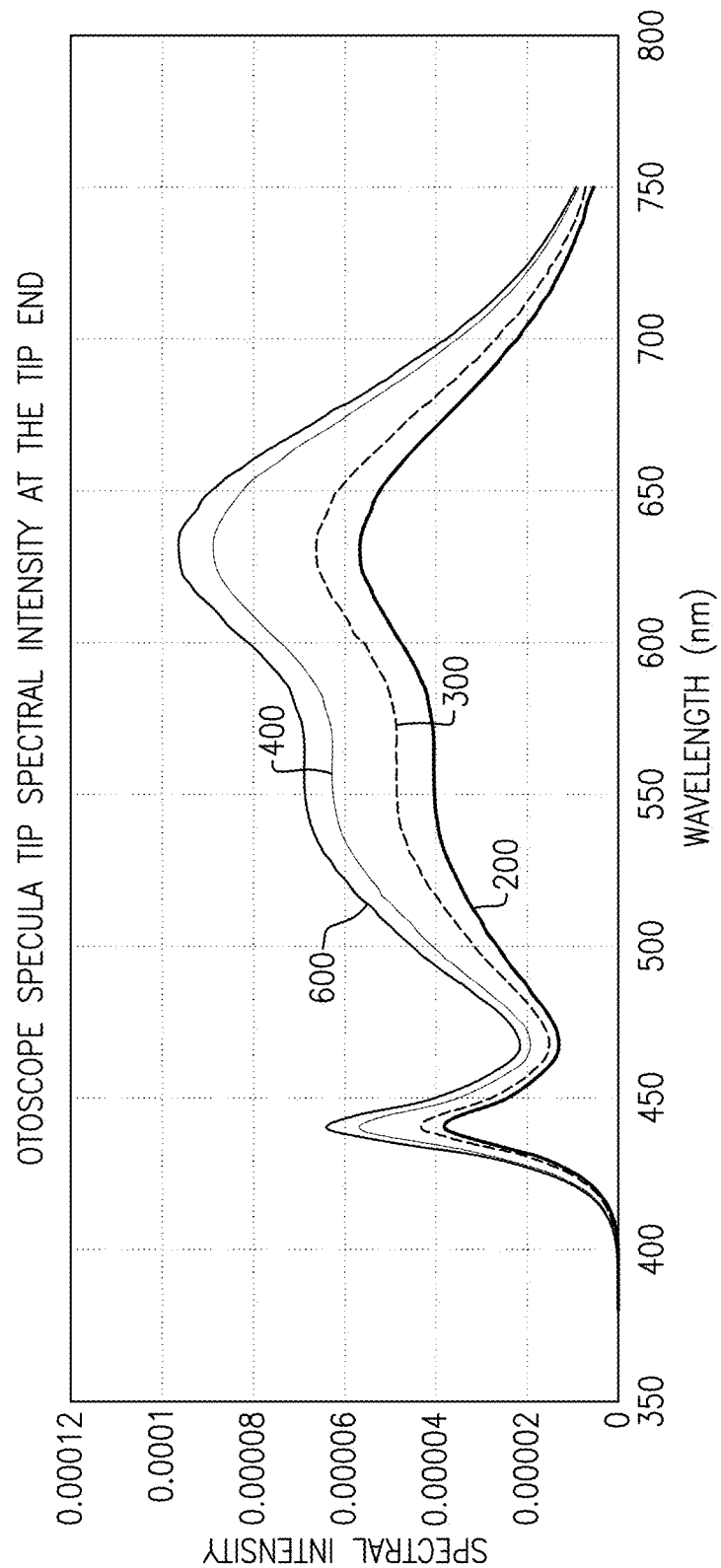
FIGS. 5 and 6 are graphical summaries of spectral intensity data taken from various speculum tip elements, including speculum tip elements made in accordance with various aspects of the invention.

Speculum tip elements 200, 300, 400 and 600 of the above enumerated Test Groups (A-C and E) are shown in FIG. 4, with representations of the light transmissibility of a representative speculum tip element being shown. A summary of the test data obtained for each Test Group is herein presented in the following Table I, with the specific data obtained for each of the individual sample speculum tip elements 200, 300, 400, 500, 600 of each Test Group A-E being provided in FIGS. 7(a)-7(j).

TABLE I

| Group | Lumens (tip end) | % of tip Light output | Lumens % (total-fiber end) | % Total Light output | Side Lumens |
|---|---|---|---|---|---|
| Test Group A (200) | 2.62 | 17.10 | 2.51 | 16.40 | −0.11 |
| Test Group B (300) | 5.76 | 37.90 | 9.12 | 59.90 | 3.36 |
| Test Group C (400) | 11.27 | 76.40 | 12.08 | 79.50 | 0.74 |
| Test Group D (500) | 10.55 | 69.20 | 12.91 | 84.40 | 2.33 |
| Test Group E (600) | 11.84 | 76.90 | 13.75 | 89.30 | 1.91 |
| No tip - bare fibers | | | 15.4 | 100 | |

For purposes of the test, the illumination output at the fiber (distal) end of the medical diagnostic device (otoscope 120, FIGS. 2, 3) was initially measured at 15.4 lumens, representing a total baseline illumination output of the device using a spectrophotometer. Each of the speculum tip elements 200, 300, 400, 500, 600 of the various Test Groups A-E were then individually attached to the otoscope 120, FIG. 2, and illumination outputs were measured using the test fixture 100 of FIGS. 2 and 3. As indicated in the foregoing Table I, the translucent green speculum tip elements 300 of Test Group B produced the greatest output of side or peripheral illumination of the speculum tip elements tested. However, this peripheral illumination was obtained at the expense of relatively large losses of total light illumination (9.12 lumens versus 15.4 lumens-59.9%), which further included a significant average loss of illumination output at the tip end (5.76 lumens versus 15.4 lumens-37.9%). Conversely, the negative percentage of peripheral illumination output represented by each of the black (control) speculum tip elements 200 (Test Group A) is believed to be the result of the absorption of light due to the black additive color of the speculum tip element 200.

The clear transparent speculum tip elements 400 (Test Group C) having polished interior and exterior surfaces efficiently transmitted light to the distal tip end (11.27 lumens vs 15.4 lumens-76.4%), but with literally no peripheral illumination output (0.74 lumens).

Each of the clear translucent speculum tip elements 500, 600 (Test Groups D and E) having a polished distal portion of the interior surface and a textured exterior surface transmitted the highest percentages of total light (84.4% and 89.30%, respectively). Surprisingly, however, these speculum tip elements 500, 600 also provided increased side or peripheral illumination outputs (2.33 lumens and 1.91 lumens, respectively), as compared to the clear transparent speculum tip elements 400 (Test Group C), having both polished interior and exterior surfaces. Still further, the speculum tip elements 600 of Test Group E also surprisingly exhibited a higher percentage of illumination being transmitted to the distal opening than any of the remaining Test Groups, including Test Group C. As noted, the specific test data for the sample tip elements 200, 300, 400, 500, and 600 of each Test Group is provided in FIGS. 7(a), 7(c), 7(e), 7(g) and 7(i) for the representative speculum tip elements 200, 300, 400, 500, and 600 shown in FIGS. 7(b), 7(d), 7(f), 7(h) and 7(j), respectively.

As previously noted, the relative light transmissive qualities are pictorially illustrated between each of the Test Groups A-E of the various speculum tip elements 200, 300, 400, 500, and 600 in FIG. 4 and FIGS. 7(b), 7(d), 7(f), 7(h), and 7(j). Though not shown, the light transmissive qualities of the speculum tip elements 500 of Text Group D are nearly identical to the illustrated speculum tip elements 600 of Test Group E. Surprisingly, it has been determined that various objectives or goals can be realized by adjusting the surface finish and/or color characteristics of the speculum tip elements. One such objective is to provide a speculum tip element design having no appreciable losses or leaks such that the total light output measured from the distal tip opening is maximized (that is the output at the distal tip opening of the speculum tip element is essentially equal to the total output from the optical fibers). Yet another objective is to maximize the light output of the speculum tip element circumferentially or peripherally. Each of these goals are preferred for different diagnostic examinations and provide flexibility, depending, for example, on the medical target to be examined.

Additional tests were conducted to determine the effects of various surface finishes relative to the interior surfaces of various speculum tip elements with the summary of results being provided in Table II. Control speculum tip elements were tested in combination with the following Test Specimens, each taken from the prior Test Group E and provided with different and specific interior surface features. More specifically, the following Test Specimens were tested:

Test Specimen 1 included a speculum tip element 600 of prior test Group E with no interior surface feature changes being made to the polished distal portion 62, FIG. 1(e). This Test Specimen was used as a control subject.

Test Specimen 2 included a speculum tip element 600 from the prior Test Group E, but in which a series of linear scratches were made to the polished distal portion 62, FIG. 1(e), of the interior surface 60, FIG. 1(e), of the speculum tip element 600.

Test Specimen 3 also included a speculum tip element 600 from the prior Test Group E, but in which the speculum tip element 600 further included a plurality of radial scratches that were applied to the polished distal portion 62, FIG. 1(e), of the interior surface 60, FIG. 1(e).

Finally, Test Specimen 4 included a speculum tip element 600 from the prior Test Group E, but in which the speculum tip element 600 was further defined by having the polished distal portion 62, FIG. 1(e) of its interior surface 60, FIG. 1(e) sandblasted, thereby creating a gray appearance.

Each of the above Test Specimens 1-4 were tested in the same test fixture 100, FIGS. 2, 3, with each of the Test Specimens 1-4 being individually and releasably attached to the distal insertion portion 126 of the otoscope 120, as supported in relation to the spherical integration chamber 104 and the external port 108. Illumination outputs were obtained using a spectrophotometer (not shown), in the same manner previously described. The total (fiber end) illumination output of the medical device (otoscope 120) used was measured at 15.5 lumens prior to attachment of each of the Test Specimens. The results obtained by this testing are summarized in the following Table II:

TABLE II

| Spec Tip | Lumens (tip end) | % of tip Light output | Lumens % (total-fiber end) | % Total Light output | Side Lumens |
|---|---|---|---|---|---|
| Test Specimen 1 | 11.84 | 76.4 | 13.75 | 88.7 | 1.91 |
| Test Specimen 2 | 9.92 | 64.0 | 12.48 | 80.5 | 2.56 |

TABLE II-continued

| Spec Tip | Lumens (tip end) | % of tip Light output | Lumens % (total-fiber end) | % Total Light output | Side Lumens |
|---|---|---|---|---|---|
| Test Specimen 3 | 8.02 | 51.7 | 11.34 | 73.2 | 3.32 |
| Test Specimen 4 | 3.05 | 19.7 | 4.4 | 28.4 | 1.35 |
| No tip - bare fibers | | | 15.5 | | |

As can be understood from the foregoing test data, all of the Test Specimens 2-4 produced significant light losses at the distal tip opening, as well as the entire (total) speculum tip element itself, as compared to the control Test Specimen 1. Higher outputs of side or peripheral illumination output were measured for Test Specimens 2 and 3, as compared to Test Specimen 1. Test Specimen 4 produced significant reductions in tip and peripheral illumination output, along with the greatest percentage of total illumination output being lost.

A similar test was performed on a speculum tip element 400 made from the prior Test Group C (using Profax 6523 homopolymer polypropylene) in which a control speculum tip element 400 (Test Specimen 5) was compared to a similar speculum tip element (Test Specimen 6), the latter having its polished interior surface roughened.

TABLE III

| Spec Tip | Lumens (tip end) | % of tip Light output | Lumens % (total-fiber end) | % Total Light output | Side Lumens |
|---|---|---|---|---|---|
| Test Specimen 5 | 11.25 | 73.2 | 12.08 | 78.6 | 0.74 |
| Test Specimen 6 | 7.45 | 48.5 | 10.01 | 65.1 | 2.56 |
| No tip - bare fibers | | | 15.37 | | |

As noted from the foregoing Tables II and III, roughening of the polished interior surface 60, of a clear speculum tip element resulted in an appreciable increase in peripheral illumination output, but significant decreases were created in both axial (tip) illumination, as well as total illumination output. Interestingly and while the impact of scratches and other surface effects creates an increase in the side (peripheral) lumen output, sandblasting of the polished interior surface 60 created decreases in all aspects (distal, total and peripheral) of illumination output.

The effects of exterior surface finish upon light transmissivity were then further evaluated using the same test fixture 100, FIGS. 2, 3. For determining these effects, three (3) additional Test Groups of speculum tip elements were evaluated. A first set (Test Group I) included speculum tip elements 600 made from the same clarified (clear) polyethylene as Test Group E, discussed previously. These speculum tip elements 600, which are made from Pinnacle 1112 polyethylene were provided in sub groups having exterior surface finishes of VDI 30, VDI 32 (31.5) and VDI 33, respectively. A second set (Test Group II) included speculum tip elements 500 made from the same material as Test Group D, Profax 6523 polyethylene, which was similarly provided into subgroups having exterior surface finishes of VDI 30, VDI 32 (31.5) and VDI 33, respectively. Finally, a third set (Test Group III) included representative speculum tip elements made from clarified Pinnacle 1112 that were similarly provided in sub groups having exterior surface finishes of VDI 30, VDI 32 (31.5) and VDI 33, respectively. Ten (10) sample speculum tip elements were provided in each subgroup of the speculum tip elements having VDI 30 and 32 finishes. Only one test sample was available for testing in the subgroup having the VDI 33 surface finish. The results of the various tests are herein summarized in the following Table IV:

TABLE IV

| Group | Lumens (tip end) | % of tip Light output | Lumens % (total-fiber end) | % Total Light output | Side Lumens |
|---|---|---|---|---|---|
| Test Group I (VDI 30) | 12.28 | 79.4 | 13.97 | 90.3 | 1.69 |
| Test Group I (VDI 32) | 12.00 | 77.1 | 13.79 | 88.5 | 1.78 |
| Test Group I (VDI 33) | 12.08 | 78.1 | 13.84 | 89.5 | 1.77 |
| Test Group II (VDI 30) | 12.77 | 82.4 | 14.31 | 92.3 | 1.54 |
| Test Group II (VDI 32) | 12.59 | 81.3 | 14.15 | 91.3 | 1.56 |
| Test Group II (VDI 33) | 12.50 | 80.8 | 14.14 | 91.3 | 1.63 |
| Test Group III (VDI 30) | 12.23 | 79.4 | 13.90 | 90.3 | 1.68 |
| Test Group III (VDI 32) | 12.16 | 76.6 | 13.75 | 86.6 | 1.59 |
| Test Group III (VDI 33) | 12.08 | 76.5 | 13.78 | 87.2 | 1.70 |

Individual data results for each of the above Test Groups I-III is provided in the attached FIGS. 8(a)-8(c), 9(a)-9(c), and 10(a)-10(c). In general, the results of the foregoing tests indicate that increasing the roughness of the exterior surface or producing barriers to light transmission produces a reduced output at the distal opening of the speculum tip element, as well as the total illumination transmitted through the speculum tip element. As can be understood from the foregoing data, the total illumination output, as well as the axial (through the distal opening) and peripheral illumination output (through the exterior surface) of a speculum tip element can be effectively tuned by controlling material properties, particularly surface finish.

Different variations of either color/tint of the moldable material and surface finishes or lack of finishes on the surfaces of the speculum tip elements have been determined to create substantial effects to the transmissibility of light.

For purposes of this invention, it has been generally determined that providing a surface finish in the fabrication of otoscopic speculum tip elements increases overall light transmissivity, particularly using a molded plastic material that includes a clarifier to create an optically clear product. Preferably, the exterior surface of these speculum tip elements is defined with a surface finish of approximately VDI 30-VDI 33, although a range of between VDI 29-VDI 36 has been determined to provide acceptable results.

Figure 6:
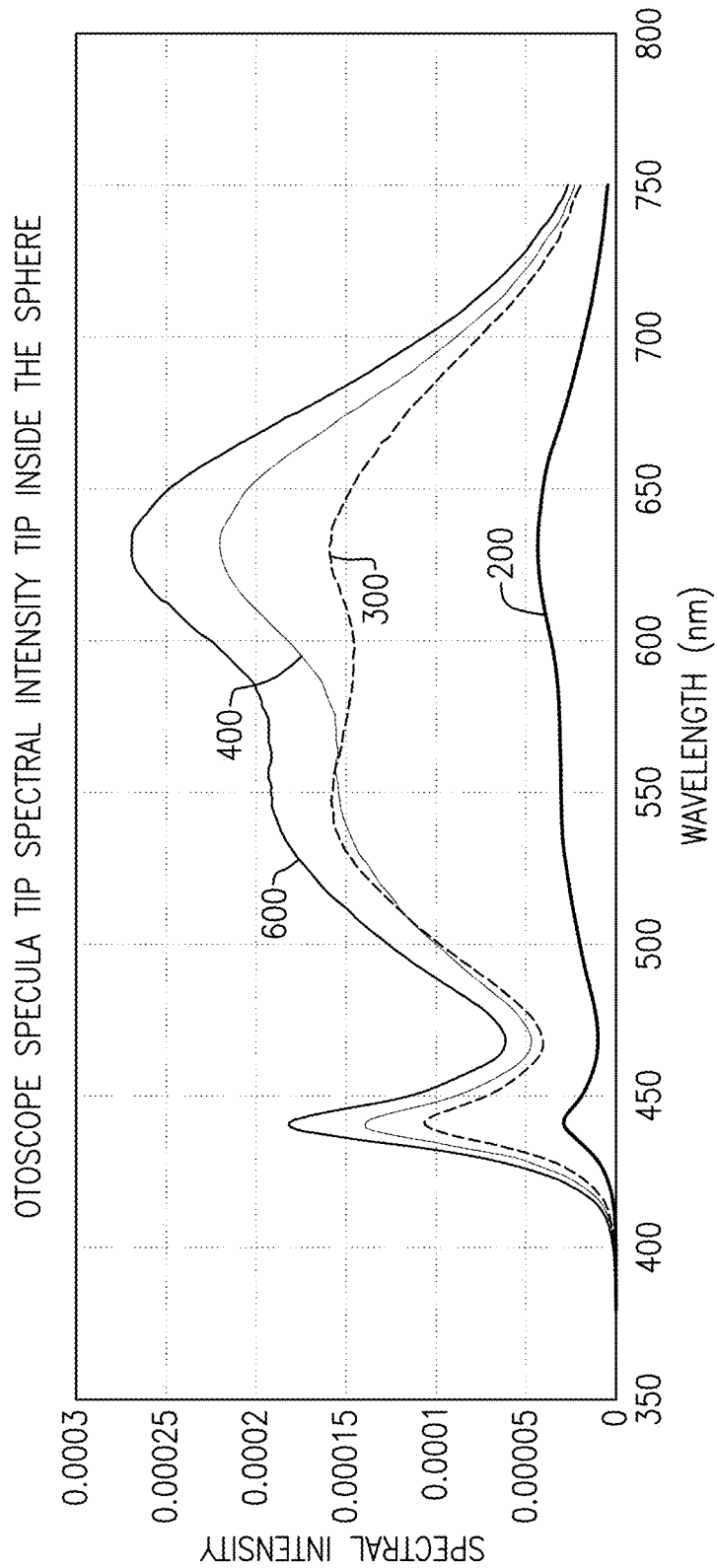
Figure 7B:
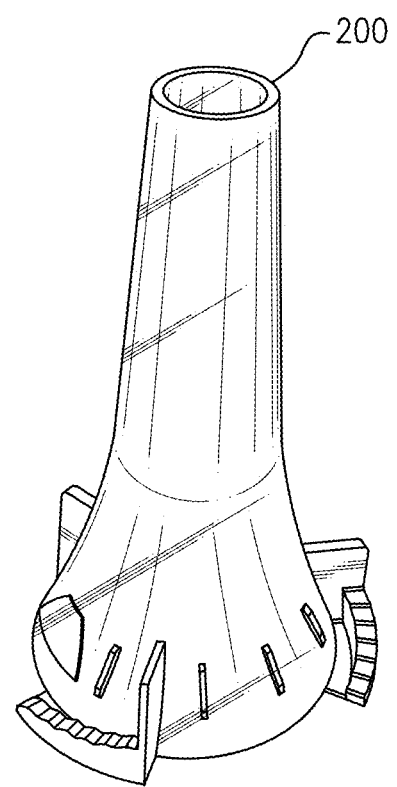
FIGS. 7(a), 7(c), 7(e), 7(g) and 7(i) present tabular data of light transmissivity of various speculum tip elements, shown as FIGS. 7(b), 7(d), 7(f), 7(h) and 7(j), respectively.
Figure 7D:
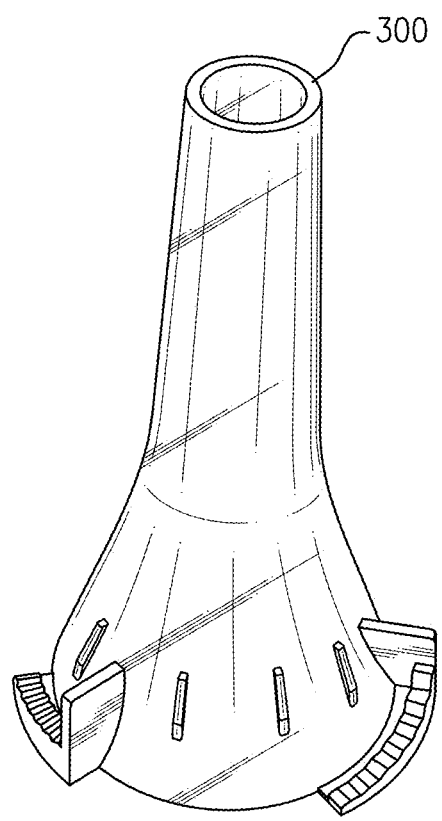
Figure 7F:
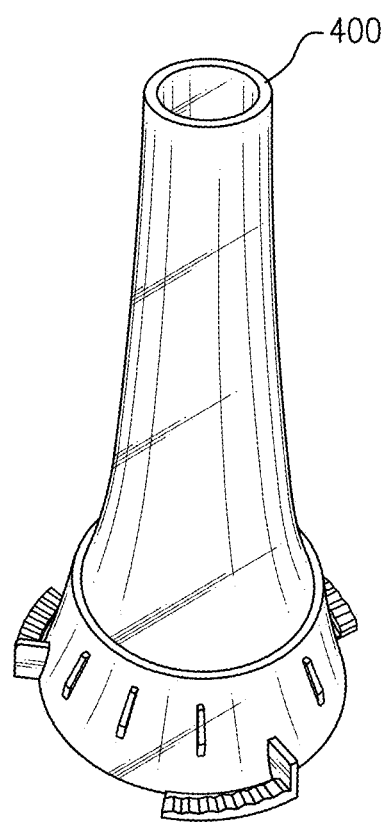
Figure 7H:
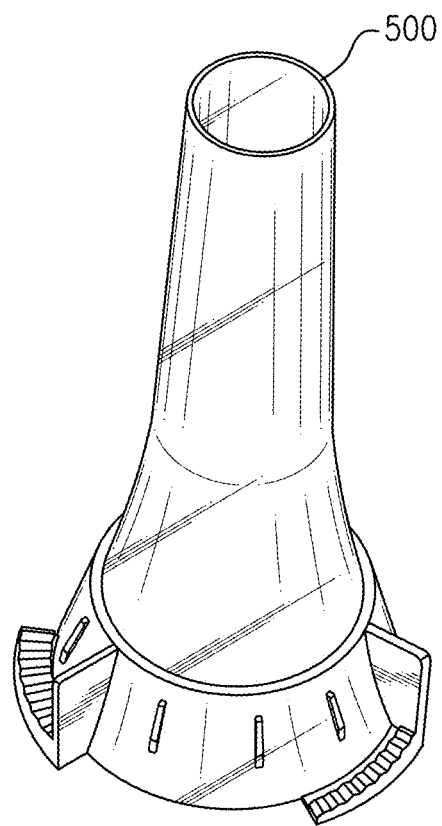
Figure 7J:
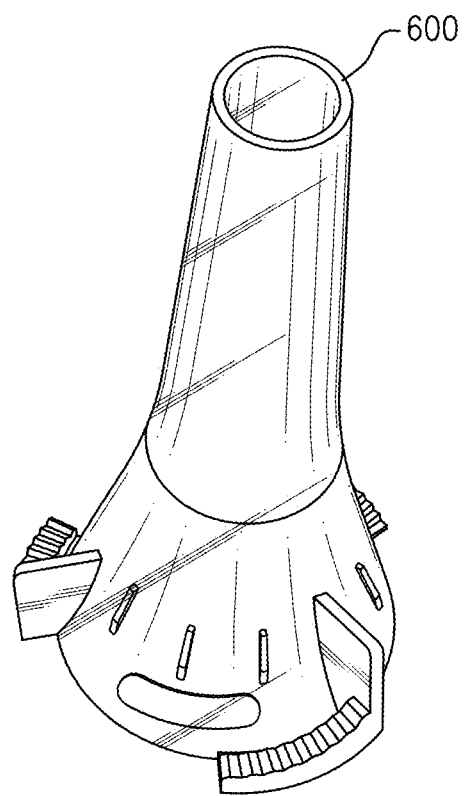

FIGS. 6 and 7 illustrate a graphical summary of spectral intensity at the distal tip end and total (inside the spherical integration chamber), respectively, for various speculum tip elements as measured using the test fixture of FIGS. 2 and 3. More specifically, FIG. 6 illustrates the spectral intensity for each of the speculum tip elements 200, 300, 500 and 600 taken over substantially the visible range of wavelengths with each speculum tip element being fully disposed within the spherical test chamber 104, as shown in FIG. 2, and with each tip element only partially disposed within the spherical chamber 104, as shown in FIG. 3. The test data from these graphs supports the test data previously obtained and reported in Table I and shown in FIG. 4 relative to the amounts of peripheral and total illumination produced, based on the surface finish and/or tint (color) of material used in each speculum tip element.

It will be understood from the preceding description that other variations and modifications of the inventive tip element design and method enable uses for literally an unlimited myriad of applications, depending on light transmissive characteristics deemed most important for purposes or uses of the specific application and in accordance with the following claims.

PARTS LIST FOR FIGS. 1(a)-10(c)

40 speculum tip element
40A speculum tip element
42 hollow body, speculum tip element
44 distal tip opening, speculum tip element
48 proximal tip opening, speculum tip element
52 engagement features, external
54 depending axial portion
55 circumferential securing portion
56 teeth, plurality
60 interior surface, speculum tip element
62 distal portion, interior surface
63 proximal portion, interior surface
64 interior protrusion
65 exterior surface, speculum tip element
66 ribs, axial
70 annular sealing ring
100 test fixture
104 spherical integration chamber
108 external port, spherical integration chamber
120 otoscope
124 instrument head
126 distal insertion portion
128 handle portion
200 speculum tip element
300 speculum tip element
400 speculum tip element
500 speculum tip element
600 speculum tip element It will be readily apparent to a person of sufficient skill that there are other variations and modifications within the intended scope of this invention, and as set forth by the following claims. In addition, the surface finishes described herein refer to VDI 3400 based on EDM. Similar effects can be provided using Moldtech (MT) or other techniques.

The invention claimed is:

1. A method for maximizing the light transmissivity of a speculum tip element, the speculum tip element having an axisymmetric hollow body including a substantially conical shape including a distal opening and a proximal opening, the method comprising:
molding the speculum tip element from a plastic material that is one of optically translucent or transparent to enable both axial and circumferential transmissivity of visible light through the distal opening and the body, respectively, the speculum tip element having an exterior surface and an interior surface;
providing the exterior surface of the speculum tip element and a proximal portion of the interior surface with a textured surface finish, in which the textured surface finish of the exterior surface is between VDI 29 and VDI 36; and
providing a distal portion of the interior surface of the speculum tip element with a smooth polished surface finish.

2. The method according to claim 1, wherein the plastic material is optically transparent.

3. The method according to claim 1, further comprising:
roughening at least the smooth polished surface finish of the distal portion of the interior surface in order to increase circumferential illumination of the speculum tip element.

4. The method according to claim 3, wherein roughening the interior surface includes adding linear or radial scratches to at least the smooth polished surface finish of the distal portion of the interior surface.

5. The method according to claim 1, in which the textured surface finish of the exterior surface is between VDI 30 and VDI 32.

6. The method according to claim 5, in which a percentage of total illumination output of the speculum tip element is greater than 80 percent of an illumination output of an attached light source.

7. The method according to claim 1, in which a percentage of peripheral illumination of the speculum tip element is greater than 10 percent of a total illumination output of the speculum tip element.

8. An speculum tip element comprising:
an axisymmetric hollow body having a substantially conical shape;
a distal opening;
an opposing proximal opening;
an interior surface having a distal portion and a proximal portion; and
an exterior surface,
the hollow body being made from a moldable plastic and having a roughened exterior surface, a roughened proximal portion of the interior surface and a smooth and polished distal portion of the interior surface and in which the plastic is at least optically translucent in order to permit light from a coupled light source to be emitted through the distal opening, as well as be emitted circumferentially from the exterior surface and in which the exterior surface has a textured surface finish between VDI 29 and VDI 36.

9. The speculum tip element according to claim 8, in which the speculum tip element is fabricated from an optically transparent plastic.

10. The speculum tip element according to claim 8, in which the hollow body is made from a colored or tinted plastic material.

11. The speculum tip element according to claim 8, in which an amount of peripheral illumination output relative to a total illumination output of the speculum tip element is more than 10 percent.

12. The speculum tip element according to claim 8, in which an amount of total illumination output of the speculum tip element is greater than 80 percent, as compared to that of the light source.

13. A speculum tip element comprising:
an axisymmetric hollow body made from a moldable plastic material;
a distal tip opening;
a proximal tip opening;
an interior surface; and
an exterior surface, the hollow body being defined by a truncated frusto-conical shape in which the distal tip opening has a diameter that is smaller than a diameter of the proximal tip opening, a distal portion of the interior surface having a smooth surface finish and a proximal portion of the interior surface and the exterior surface having a roughened textured surface finish such that light from a light source of an otoscope can be axially directed through the axisymmetric hollow body for emission through the distal tip opening, as well circumferentially through the exterior surface and wherein the textured surface finish of the exterior surface is between VDI 29 and VDI 36.

14. The speculum tip element according to claim 13, in which the axisymmetric hollow body is made from one of an optically transparent or optically translucent plastic material.

15. The speculum tip element according to claim 6, in which an amount of peripheral illumination output relative to a total illumination output of the speculum tip element is more than 10 percent.

16. The speculum tip element according to claim 6, in which an amount of total illumination output of the speculum tip element is greater than 80 percent, as compared to that of the light source.

* * * * *

UNITED STATES PATENT AND TRADEMARK OFFICE
CERTIFICATE OF CORRECTION

| | | |
|---|---|---|
| PATENT NO. | : 11,399,709 B2 | Page 1 of 1 |
| APPLICATION NO. | : 16/820000 | |
| DATED | : August 2, 2022 | |
| INVENTOR(S) | : Robert L. Vivenzio and Raymond A. Lia | |

It is certified that error appears in the above-identified patent and that said Letters Patent is hereby corrected as shown below:

In the Claims

Claim 13:
Column 15
Line 21 change "a roughened textured" to --a textured--

Signed and Sealed this
Seventeenth Day of January, 2023

Katherine Kelly Vidal
*Director of the United States Patent and Trademark Office*